United States Patent [19]
Ooms et al.

[11] Patent Number: 5,994,584
[45] Date of Patent: Nov. 30, 1999

[54] PROCESS FOR THE PREPARATION OF 4-AMINODIPHENYLAMINE

[75] Inventors: Pieter Ooms, Krefeld; Henrey Giera, Bergisch Gladbach, both of Germany

[73] Assignee: Bayer Aktiengesellschaft, Leverkusen, Germany

[21] Appl. No.: 09/264,201

[22] Filed: Mar. 8, 1999

[30] Foreign Application Priority Data

Mar. 13, 1998 [DE] Germany .............................. 198 10 929

[51] Int. Cl.$^6$ ................................................. C07C 209/00
[52] U.S. Cl. .......................... 564/416; 564/415; 564/433; 564/434
[58] Field of Search .................... 564/415, 416, 564/433, 434

[56] References Cited

U.S. PATENT DOCUMENTS

| | | |
|---|---|---|
| 4,187,243 | 2/1980 | Shaffer et al. . |
| 4,187,249 | 2/1980 | Maender et al. . |
| 4,665,232 | 5/1987 | Podder et al. . |
| 4,670,595 | 6/1987 | Podder et al. . |
| 4,683,332 | 7/1987 | Sturm . |
| 5,420,354 | 5/1995 | Malz et al. . |
| 5,574,187 | 11/1996 | Malz et al. . |
| 5,739,403 | 4/1998 | Reinartz et al. .......................... 564/423 |

FOREIGN PATENT DOCUMENTS

| | | |
|---|---|---|
| 2244391 | 2/1999 | Canada . |
| 185683 | 5/1906 | Germany . |
| 93/00324 | 1/1993 | WIPO . |
| 93/24450 | 12/1993 | WIPO . |

OTHER PUBLICATIONS

Kirk–Othmer Ency. of Chemical Technology, 4th ed., (month unavailable) 1992, vol. 3., pp. 424–456.

Chem. Ind., (month unavailable), 1994, Catalysis of Organic Reactions, pp. 137–149.

Hauben–Weyl, Methoden der organische Chemie Vale, 16a, Part 2, p. 1015ff, (month unavailable) 1990.

Chemical Reviews 80, 1980, p. 429ff.

Kirk–Othmer Encyc. Of Chemical Tech., vol. 9, p. 57ff, 1990.

Ullmann's Encyc. of Industrial Cheimistry, 5th edition, (date unavailable).

*Primary Examiner*—Paul J. Killos
*Attorney, Agent, or Firm*—Joseph C. Gil; Diderico Van Eyl

[57] ABSTRACT

4-Aminodiphenylamines are prepared by hydrogenating nitrosobenzene or mixtures of nitrosobenzene and nitrobenzene with hydrogen in the presence of fluorides and heterogeneous catalysts in inert aprotic solvents at temperatures from 0 to 200° C. and pressures from 0.1 to 150 bar.

9 Claims, No Drawings

PROCESS FOR THE PREPARATION OF 4-AMINODIPHENYLAMINE

BACKGROUND OF THE INVENTION

The invention relates to a process for the preparation of 4-aminodiphenylamine (4-ADPA) by hydrogenation of nitrosobenzene with hydrogen in the presence of hydrogenation catalysts and fluorides.

4-ADPA is an important intermediate for antioxidants and stabilisers in the rubber and polymer industry (Kirk-Othmer, Encyclopedia of Chemical Technology, 4th Edition, 1992, Vol. 3, p 424–447 and p 448–456; Ullmann's Encyclopedia of Industrial Chemistry, 5th Edition, Vol. A3, 1985, p 91–111).

4-Aminodiphenylamine may be prepared by various methods. One possible route to 4-ADPA is the two-stage (intermediate: 4-nitrodiphenylamine) reaction of aniline or aniline derivatives with p-nitrochlorobenzene in the presence of an acid acceptor or a neutralising agent and optionally in the presence of a catalyst. The preparation by this method is described, for example, in DE-A 35 01 698, DE-A 18 56 63, U.S. Pat. No. 4,670,595, U.S. Pat. No. 4,187,249, U.S. Pat. No. 4,468,333 and U.S. Pat. No. 4,187,248. A disadvantage of such a process is that the salts thereby obtained have to be disposed of at considerable cost. Consequently, aniline or corresponding aniline derivatives have been reacted with nitrobenzene in the presence of tetraalkylammonium hydroxides and in the presence of controlled quantities of protic materials. 4-ADPA was obtained in a satisfactory quantity in this case (see WO 95/00 324 and WO 93 24 450). According to U.S. Pat. No. 5,420,354, 4-ADPA may be obtained by reaction of aniline, nitrobenzene and hydrogen in the presence of a hydrogenation catalyst, hydrogenation inhibitor and acid cocatalyst, albeit in rather unsatisfactory yields. U.S. Pat. No. 5,574,187 describes a method for obtaining 4-ADPA by reacting aniline with nitrosobenzene or phenylhydroxylamine in the presence of acids.

These processes have the disadvantage, however, that two different starting products are used which have to be prepared in upstream, separate process stages, this being rather uneconomic.

It is also known that the hydrogenation of nitrosobenzene by way of heterogeneous catalysts yields chiefly aniline and hydrazobenzene. 4-ADPA is not mentioned as a product (Chem. Ind. 1994, Catalysis of Organic Reactions, p 137–149).

Surprisingly, it has now been found that 4-ADPA may be obtained in industrially useful yields by hydrogenation of nitrosobenzene in the presence of fluorides and heterogeneous catalysts.

The present invention therefore provides a process for the preparation of 4-aminodiphenylamine which is characterised in that nitrosobenzene or mixtures of nitrosobenzene and nitrobenzene are hydrogenated with hydrogen in the presence of fluorides and heterogeneous catalysts and in the presence of inert aprotic solvents at temperatures from 0 to 200° C. and pressures from 0.1 to 150 bar.

Fluorides suitable for the process according to the invention are inorganic fluorides, such as alkali metal fluorides, alkaline earth metal fluorides and the corresponding fluorides of the elements 58 to 71 of the periodic system of elements (according to IUPAC, new). Examples include: the fluorides of sodium, potassium, lithium, caesium, rubidium, magnesium, calcium, barium, lanthanum and/or cerium, particularly the fluorides of lithium, sodium, potassium, caesium, more particularly preferably potassium fluoride, caesium fluoride, sodium fluoride.

SUMMARY OF THE INVENTION

Organic bases are also suitable, such as, for example, quaternary alkylammonium fluorides ($NR_4^+F^-$ with R independently of one another for alkyl, aryl or aralkyl with 1 to 8 carbon atoms). Examples include: tetramethylammonium fluoride, tetraethylammonium fluoride, tetrapropylammonium fluoride, tetrabutylammonium fluoride, tetrapentylammonium fluoride, tetrahexylammonium fluoride, tetraheptylammonium fluoride, tetraoctyl-ammonium fluoride, methyltributylammonium fluoride, methyltripropylammonium fluoride, methyltriethylammonium fluoride, trimethylbenzylammonium fluoride. Tetramethylammonium fluoride, tetraethylammonium fluoride, tetrapropyl-ammonium fluoride and tetrabutylammonium fluoride are particularly preferred. The use of tetramethylammonium fluoride, tetraethylammonium fluoride and tetrabutylammonium fluoride is more particularly preferred.

Any mixtures of the above-mentioned fluorides may also be used.

Such fluorides and preparation processes for such compounds from intermediates such as, for example, oxides, hydroxides, bromides or chlorides are described in Kirk-Othmer, Encyclopedia of Chemical Technology, Edition, Vol. 9, p 527 ff, New York 1966, Houben-Weyl, Methoden der organischen Chemie, Vol. E, 16 a, Part 2, p 1015 ff, Stuttgart 1990 and Chemical Reviews 80 (1980), p 429 ff.

It is also possible to use the inorganic fluorides in conjunction with phase transfer catalysts. Suitable phase transfer catalysts are described, for example, in W. E. Keller, Fluka-Kompendium, Vol. 1, 2, 3, Georg Thieme Verlag, Stuttgart 1986, 1987, 1992. For example, the above-mentioned fluorides may be used together with crown ethers, such as 18-crown-6 or quaternary ammonium compounds.

The fluorides to be used according to the invention may have a water content of up to 6 moles of water, preferably up to 5 moles of water, particularly preferably up to 4 moles of water, based on one mole of fluoride.

The fluorides according to the invention may be added to the reaction mixture in solid form, as a melt or as a solution in an aprotic solvent or in a mixture of nitrosobenzene and one or more aprotic solvents.

DETAILED DESCRIPTION OF THE INVENTION

The fluorides are used in a quantity from 0.01 to 3, preferably 0.1 to 2, particularly 0.3 to 1.5 equivalents per mole of nitrosobenzene.

According to the invention, the above-mentioned fluorides may be used in the pure form or deposited on a support such as, for example, $Al_2O_3$, $SiO_2$ or polymer resin.

Suitable inert aprotic solvents are aromatic hydrocarbons with 6 to 20 carbon atoms, linear or cyclic ethers with up to 5 oxygen atoms and 2 to 16 carbon atoms, aromatic halogenated hydrocarbons with 6 to 20 carbon atoms and amides with 1 to 10 carbon atoms. Of course, the above-mentioned solvents may be used in mixture. Suitable solvents include, in particular: benzene, toluene, xylene, tert.-butylmethylether, tert.-amylmethylether, diisopropylether, diethylene glycol dimethylether, glycoldimethylether, dioxane, tetrahydrofuran, diamylether, chlorobenzene, dichlorobenzene, dimethylformamide, dimethylacetamide and N-methylpyrrolidinone. The following are used in preference: toluene, xylene, glycoldimethylether, dioxane, tetrahydrofuran, tert.-butylmethylether, diisopropylether, diethylene glycol dimethylether, particularly tert.-butylmethylether, diethylene glycol dimethylether, glycol dimethylether, dioxane, tetrahydrofuran and toluene. The quantity of solvent is not critical for the process according to the invention and depends particularly on the reaction temperature and on the type and quantity of fluorides and catalysts used. The solvents are usually used in quantities from 1 to 99 wt. %, preferably 5 to 95 wt. %, particularly preferably 15 to 90 wt. %, based on the total quantity of the reaction mixture.

Heterogeneous catalysts suitable for the process according to the invention are practically all the heterogeneous catalysts which are known for hydrogenation reactions. The catalysts according to the invention include metals of the 8–10 group of the periodic system (according to IUPAC, new) or copper and/or chromium on a suitable support with a metal content from 0.01 to 50 wt. %, preferably 0.1 to 10 wt. %, based on the total weight of the catalyst. According to the invention, it is possible to use catalysts containing one or more of the above-mentioned metals. If several elements are present, the stated proportions by weight apply to the sum of the individual proportions. Preferred metals are, in particular, platinum, palladium, rhodium and ruthenium; platinum, palladium and rhodium are particularly preferred. Other preferred catalysts are Raney nickel and supported nickel catalysts.

According to the invention, the above-mentioned metals or their compounds may also be used in the pure form as a solid. Examples of a metal in the pure form include palladium black and platinum black.

The catalysts according to the invention may be prepared by various methods which are known to the skilled person. For example, solutions of one or more of the metal compounds mentioned may be deposited on the catalyst support to be used according to the invention by, for example, soaking, adsorption, dipping, spraying, impregnating and ion exchange. Further elements may be added to the catalyst in a known manner and way. It is also possible to fix one or more of the metals mentioned to the support by precipitation with a base. Suitable bases include e.g. alkali(ne earth) metal hydroxides. One or more metals may be deposited on the support both successively in any order and simultaneously. A special embodiment of the invention consists in depositing the metal by precipitation of a metal halide or a metal halide complex compound with a suitable base and reduction of the metal compound to the metal. In one embodiment, if the supports are prepared by means of the sol-gel process, solutions of one or more of the metal compounds mentioned may be added to the sol in a manner known to the skilled person.

Suitable materials for the use according to the invention as catalyst supports are all the industrially conventional catalyst supports based on carbon, element oxides, element carbides or element salts in various forms of use. Examples of carbon-containing supports are coke, graphite, carbon black or activated carbons. Examples of element oxide catalyst supports are $SiO_2$ (natural or synthetic silica, quartz), $Al_2O_3$, ($\alpha$-, $\gamma$-$Al_2O_3$), aluminas, natural and synthetic aluminosilicates (zeolites), layer silicates such as bentonite and montmorillonite, $TiO_2$ (rutile, anatase), $ZrO_2$, MgO or ZnO. Examples of element carbides and salts are SiC, $AlPO_4$, $BaSO_4$, $CaCO_3$. In principle, both synthetic materials and supports from natural sources such as e.g. pumice stone, kaolin, bleaching earths, bauxites, bentonites, diatomaceous earth, asbestos or zeolites may be used.

Further suitable supports for the catalysts which may be used according to the invention are element mixed oxides and hydrated oxides of elements of groups 2 to 16 of the periodic system and of the rare earth metals (atomic numbers 58 to 71), preferably of the elements Al, Si, Ti, Zr, Zn, Mg, Ca, Zn, Nb and Ce which may be produced, i.a. by way of mechanical mixing operations, joint precipitation of salts or by means of co-gels of salts and/or alkoxides, as the skilled person knows.

Examples of mixed oxides are magnesium aluminium oxides (hydrotalcites).

The supports may be used both within the meaning of chemically uniform pure substances and in mixture. Catalysts suitable for the use according to the invention are materials in both lump and powder form. If the supported catalyst is arranged as a fixed bed, the support is used preferably as moulded articles, e.g. as spheres, cylinders, rods, hollow cylinders, rings etc. Optionally, catalyst supports may be modified further by extrusion, tabletting, optionally with the addition of further catalyst supports or binders such as $SiO_2$ or $Al_2O_3$, and calcination. The internal surface area of the supports (BET surface) is 1 to 2,000 $m^2$/g, preferably 10 to 1,600 $m^2$/g, more particularly 20 to 1,500 $m^2$/g. The preparation and further processing of the catalyst supports used according to the invention are likely to be well known to the skilled person and represent the state of the art.

Activated carbons and Si-, Al-, Mg-, Zr- and Ti-containing materials are used in preference as support materials, activated carbon and supports containing silicon, magnesium and aluminium being particularly preferred.

The catalysts according to the invention may be used in batchwise process variants in quantities from 0.01 to 20 wt. %, based on nitrosobenzene used, preferably in quantities from 0.01 to 10 wt. %. If the reaction is carried out continuously, for example, in an agitated reactor with a catalyst in powder form, or in the trickle phase on a fixed bed catalyst, loadings from 0.01 to 500 g of nitrosobenzene per g of catalyst and per hour may be used. Loadings from 0.02 to 300 g of nitrosobenzene per g of catalyst and per hour are preferred.

Nitrosobenzene or nitrosobenzene/nitrobenzene mixtures, of the kind obtained, for example, during the preparation of nitrosobenzene from nitrobenzene, may be used in the process according to the invention. The nitrosobenzene content may be, for example, 0.5 to 99%, preferably 0.5 to 98%, particularly preferably 1 to 97%.

The reaction temperatures in the process according to the invention are preferably 0 to 200° C., particularly 25 to 150° C.; the pressures (hydrogen pressure) are 0.1 to 150 bar, particularly 0.5 to 70 bar, more particularly 1 to 50 bar.

It is possible to carry out the reaction at a constant temperature and at a constant hydrogen pressure; hydrogen pressure and temperature may also, however, be altered during the course of the reaction or they may be different in different reactors. In a batchwise operation, nitrosobenzene, catalyst, solvent and fluoride may be fed into the reactor in any order. The hydrogen feed may be discontinued after a certain quantity has been fed in, and optionally resumed at a later stage.

Continuous process variants are, for example, hydrogenation in the liquid phase with a suspended catalyst in the form of a powder (slurry), hydrogenation in the trickle phase on a fixed bed catalyst, or hydrogenation with a suspended catalyst in a bubble column. The reaction may be carried out in equipment known to the skilled person for contacting solid, liquid and gas phases. In particular, agitated reactors, pump-circulated reactors, bus reactors, bubble columns operated in co- or counter-current, or trickle phase reactors or cascades of said reactors are suitable in this context, whereby the various types of reactors may also be present at the same time in a cascade.

If the catalyst is used as a powder in the liquid phase, the agitated vessels to be used are provided with suitable stirrers in order to mix the reaction components. Blade agitators, multi-stage impulse counter-current agitators, propeller, anchor or gas injection agitators may be used.

The substances also obtained during the process according to the invention are intermediates of the hydrogenation of nitrosobenzene to aniline and may be converted without residue to aniline which is likewise a valuable starting product for the synthesis of many industrial end products.

The invention is further described in the following illustrative examples. All parts and percentages are by weight, unless otherwise noted.

EXAMPLES

The following examples demonstrate the feasibility of the reaction at various temperatures and using various catalysts, fluorides and solvents. The reaction products were analysed by gas chromatography (Durabond DB-5-MS; 30 m×0.25 mm ID) with the internal standard n-tridecane and by quantitative HPLC. The conversion to nitrosobenzene was complete in all the tests described. Work up and sample preparation was carried out under nitrogen.

The fluorides and catalysts used are commercial products or were prepared in the manner described below.

Preparation of the catalyst Pt/activated carbon

A slurry of 475 g of activated carbon (Norit-B-Supra, Norit) was prepared in 2,600 ml of deionised water, the mixture was heated to 50° C. and a solution of 87.5 g of sodium formate in 400 ml of deionised water was added. Over a period of 30 minutes a mixture of 100 g of an $H_2PtCl_4$ solution (25 wt. % of Pt) and 400 ml of deionised water was added dropwise and stirring was continued for one hour at 50° C. The catalyst was then removed by suction, washed and dried under vacuum at 60° C.

EXAMPLES 1 to 12 (hydrogenations under normal pressure)

EXAMPLES 1

A charge of 65 ml of diethylene glycol dimethylether, 17.4 g (0.055 moles) of $(H_9C_4)_4NF.3H_2O$ from Fluka and 0.5 g of 5% Pd/C catalyst 3230 in powder form from Engelhard was placed in a nitrogen-flushed 250 ml flat-ground vessel with gas injection agitator and heated to 80° C. After this temperature was reached, the nitrogen was replaced at normal pressure by a stream of hydrogen of 25 l/h, and 5.89 g (0.055 moles) of nitrosobenzene in 10 ml of diethylene glycol dimethylether were added at the same time. After 1 h a sample was taken, filtered, neutralised with acetic acid and analysed by quantitative gas chromatography. The conversion to nitrosobenzene was complete. The 4-ADPA yield was 11.7% (the percentages are mole-% based on nitrosobenzene).

EXAMPLE 2

Example 1 was repeated with 0.5 g of a 5% Pt/C catalyst in powder form in 75 ml of monoglyme as solvent at 40° C. After a reaction period of 18 h, the 4-ADPA yield was 15.1%.

EXAMPLE 3

Example 1 was repeated with the same catalyst and $(H_9C_4)_4$ NF in 75 ml of tetrahydrofuran from Aldrich at 40° C. After a reaction period of 18 h, the 4-ADPA yield was 15.6%.

EXAMPLE 4

Example 1 was repeated with the same catalyst in 75 ml of toluene as solvent at 80° C. After a reaction period of 1 h the 4-ADPA yield was 13.1%.

EXAMPLE 5

Example 1 was repeated with the same catalyst at 40° C. After a reaction period of 90 min the 4-ADPA yield was 12.1%.

EXAMPLE 6

Example 1 was repeated with 8.0 g of 40% $KF/Al_2O_3$ from Aldrich at 80° C. After a reaction period of 2 h the 4-ADPA yield was 1.7%.

EXAMPLE 7

Example 1 was repeated with 8.4 g (0.055 moles) of CsF from Aldrich at 80° C. After a reaction period of 14 h the 4-ADPA yield was 1%.

EXAMPLE 8

Example 1 was repeated with 9.1 g (0.055 moles) of $(H_3C)_4NF.4H_2O$ from Fluka at 80° C. After a reaction period of 30 min the 4-ADPA yield was 1%.

EXAMPLE 9

Example 1 was repeated with 10.2 g (0.055 moles) of $(H_5C_2)_4NF.2H_2O$ from Fluka at 80° C. After a reaction period of 2 h the 4-ADPA yield was 9.3%.

EXAMPLE 10

Example 1 was repeated with 10.3 g (0.055 moles) of $H_5C_6CH_2(H_3C)_3NF.H_2O$ from Fluka at 80° C. After a reaction period of 6 h the 4-ADPA yield was 4.6%.

EXAMPLE 11

Example 1 was repeated with 7 g of Amberlyst 26 ($F^-$ form), a fluoride on a polymer support from Aldrich, at 80° C. After a reaction time of 90 min, the 4-ADPA yield was 1.4%.

EXAMPLE 12

Example 1 was repeated with a mixture of 2.36 g (0.022 moles) of nitrosobenzene and 2.71 g (0.022 moles) of nitrobenzene at 80° C. After a reaction period of 30 min the 4-ADPA yield was 4.7%.

Although the invention has been described in detail in the foregoing for the purpose of illustration, it is to be understood that such detail is for that purpose and that variations can be made therein by those skilled in the art without departing from the spirit and scope of the invention.

We claim:

1. A process for the preparation of 4-aminodiphenylamine, comprising hydrogenating nitrosobenzene or mixtures of nitrosobenzene and nitrobenzene with hydrogen in the presence of (i) a fluoride component, (ii) a heterogenous catalyst component (iii) an inert aprotic solvent component at a temperature ranging from 0 to 200° C. and at a pressure ranging from 0.1 to 150 bar.

2. A process according to claim 1, wherein hydrogenation is carried out at temperatures from 25 to 150° C. and pressures from 0.5 to 70 bar.

3. A process according to claim 1, wherein the fluoride component comprises a fluoride selected from the group consisting of alkali metal fluorides, alkaline earth metal fluorides, the corresponding fluorides of the elements 58 to 71 of the periodic system of elements (according to IUPAC, new), quaternary alkylammonium fluorides, and any of the foregoing fluorides deposited on a support.

4. A process according to claim 1, wherein the fluoride component is used in quantities from 0.01 to 3 equivalents per mole of nitrosobenzene.

5. A process according to claim 1, wherein the aprotic solvent component comprises a component selected from the group consisting of aromatic hydrocarbons with 6 to 20 carbon atoms, linear or cyclic ethers with up to 5 oxygen atoms and 2 to 16 carbon atoms, aromatic halogenated hydrocarbons with 6 to 20 carbon atoms and amides with 1 to 10 carbon atoms.

6. A process according to claim 1, wherein the inert solvent component is used in an amount from 1 to 99 wt. %, based on the total quantity of reaction mixture.

7. A process according to claim 1, wherein the heterogenous catalyst component comprises a catalyst selected from the group consisting of metals of the 8th to 10th group of the periodic system (according to IUPAC, new), copper, chromium, and any of the foregoing catalysts deposited on a support.

8. A process according to claim 1, wherein the catalyst component is used in a batchwise operation in quantities from 0.01 to 20 wt. %, based on nitrosobenzene used.

9. The process according to claim 8, wherein the catalyst component in a continuous operation, and loadings from 0.01 to 500 g of nitrosobenzene per g of catalyst and per hour are used.

* * * * *